(12) United States Patent
Park et al.

(10) Patent No.: US 10,696,752 B2
(45) Date of Patent: Jun. 30, 2020

(54) METHOD FOR PREPARING DIGESTION-RESISTANT MALTODEXTRIN

(71) Applicant: SAMYANG CORPORATION, Seoul (KR)

(72) Inventors: Ji Won Park, Seongnam (KR); Sung Won Park, Daejeon (KR); Chong Jin Park, Daejeon (KR)

(73) Assignee: SAMYANG CORPORATION, Seoul (KR)

( * ) Notice: Subject to any disclaimer, the term of this patent is extended or adjusted under 35 U.S.C. 154(b) by 613 days.

(21) Appl. No.: 15/378,518

(22) Filed: Dec. 14, 2016

(65) Prior Publication Data

US 2017/0335020 A1 Nov. 23, 2017

(30) Foreign Application Priority Data

May 19, 2016 (KR) .................. 10-2016-0061264

(51) Int. Cl.
  *C08B 30/18* (2006.01)
  *C12P 19/14* (2006.01)
  *C12P 19/04* (2006.01)

(52) U.S. Cl.
  CPC .............. *C08B 30/18* (2013.01); *C12P 19/04* (2013.01); *C12P 19/14* (2013.01)

(58) Field of Classification Search
  None
  See application file for complete search history.

(56) References Cited

U.S. PATENT DOCUMENTS

| | | | | |
|---|---|---|---|---|
| 5,264,568 A | * | 11/1993 | Yamada | C12P 19/14 127/32 |
| 5,364,652 A | * | 11/1994 | Ohkuma | A23C 9/13 426/549 |
| 9,353,392 B2 | * | 5/2016 | Maeda | C12P 19/02 |
| 2013/0030167 A1 | | 1/2013 | Wang et al. | |
| 2018/0094082 A1 | * | 4/2018 | Dou | C08B 30/18 |

FOREIGN PATENT DOCUMENTS

| | | | |
|---|---|---|---|
| CN | 103194509 A | | 10/2013 |
| CN | 103725732 A | * | 4/2014 |
| JP | 2006-149369 A | | 6/2006 |
| JP | 2015-181472 A | | 10/2015 |
| KR | 135075 B1 | | 4/1998 |
| KR | 10-0243525 B1 | | 2/2000 |
| KR | 10-2015-0111845 A | | 10/2015 |

* cited by examiner

*Primary Examiner* — Robert J Yamasaki (57) ABSTRACT

Disclosed herein is a method of preparing digestion-resistant maltodextrin from roasted dextrin. The method includes introducing activated carbon to be reacted with roasted dextrin after saccharification of the roasted dextrin and before filtration of the roasted dextrin.

7 Claims, 6 Drawing Sheets
(3 of 6 Drawing Sheet(s) Filed in Color)

Comparative Example 1

Fig. 8B

Comparative Example 2

Fig. 8C

Example 1

Fig. 8D

Example 2

Comparative Example 1   Comparative Example 2        Example 1         Example 2

Fig. 10

METHOD FOR PREPARING DIGESTION-RESISTANT MALTODEXTRIN

BACKGROUND

1. Technical Field

The present disclosure relates to a method of preparing digestion-resistant maltodextrin.

2. Description of the Related Art

Figure 1:
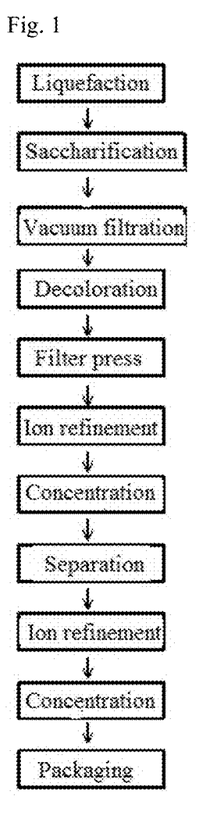
FIG. 1 is a flowchart of a typical method of preparing digestion-resistant maltodextrin.

A typical method of producing digestion-resistant maltodextrin is shown in FIG. 1.

Specifically, a typical method of producing digestion-resistant maltodextrin sequentially includes vacuum filtration after liquefaction and saccharification, decoloration, filter press filtration, ion refinement, concentration, and packaging. Vacuum filtration is aimed at filtering out insoluble substances having a large particle size, such as cornhusk, using perlite having a large particle size, and filter press filtration is aimed at filtering out fine particles of activated carbon used in decoloration using perlite having a small particle size.

However, when digestion-resistant maltodextrin is prepared in the aforementioned order, fine particles inherent to roasted dextrin, which is a raw material for digestion-resistant maltodextrin, penetrate a layer of perlite coated on a vacuum filter without being filtered out by the perlite, causing malfunction of the filter and thus significant reduction in filtration rate. As a result, it takes a long time to produce digestion-resistant maltodextrin. In addition, consumption of perlite, which is a main factor of increasing production costs, is 3 to 4 times the consumption of perlite in preparation of other starch sugars or dextrin products, causing increase in production costs and low economic feasibility.

In order to overcome these problems, there has been proposed a method in which vacuum filtration, which is a primary filtration process, is omitted or the amount of activated carbon used in decoloration before filter press filtration, which is a secondary filtration process, is considerably reduced to prevent overload of a filter press. However, this method has a problem in that insufficient decoloration can have adverse influence on conductivity and color in a subsequent ion refinement process, causing deterioration in product quality. In other words, when filter press filtration is performed after vacuum filtration and treatment with activated carbon as in a typical digestion-resistant maltodextrin preparation method, a filter press is likely to be overloaded, causing many problems. In addition, in preparation of a general starch sugar product, perlite of a filter press is replaced every time 60 t to 600 t (in terms of solid content) of the starch sugar product has been passed though the filter press, given that activated carbon is used in an amount of 0.1% to 0.5% based on total solids. However, in preparation of digestion-resistant maltodextrin, activated carbon must be used in an amount of 5% or more based on total solids, and perlite of a filter press thus needs to be replaced every time 6 t to 6.4 t (in terms of solid content) of roasted dextrin has been passed though the filter press, causing more serious overload of the filter press than in preparation of other starch sugars.

As described above, since a typical digestion-resistant maltodextrin preparation method requires frequent replacement of a filter press, the method is economically infeasible when used in mass production and is likely to increase workload of filter press cleaners.

Therefore, there is a need for an improved method of preparing digestion-resistant maltodextrin in the starch sugar industry.

BRIEF SUMMARY

Embodiments of the present disclosurehave been conceived to solve such a problem in the art and provide a method of preparing digestion-resistant maltodextrin which includes an improved filtration process capable of preventing overload of a filter and thus can produce maltodextrin efficiently and economically.

In accordance with one aspect of the present disclosure, a method of preparing digestion-resistant maltodextrin from roasted dextrin includes: introducing activated carbon after saccharification of roasted dextrin and before filtration of the saccharified roasted dextrin.

In accordance with another aspect of the present disclosure, a method of preparing digestion-resistant maltodextrin from roasted dextrin includes: a) liquefying roasted dextrin; b) saccharifying the roasted dextrin; c) introducing activated carbon and reacting the activated carbon with the roasted dextrin having been liquefied and saccharified; and d) filtering the reacted roasted dextrin.

In accordance with a further aspect of the present disclosure, there is provided digestion-resistant maltodextrin prepared by the method of preparing digestion-resistant maltodextrin as set forth above.

BRIEF DESCRIPTION OF THE DRAWINGS

The patent or application file contains at least one drawing executed in color. Copies of this patent or patent application publication color drawing(s) will be provided by the Office upon request and payment of necessary fee.

The above and other aspects, features, and advantages of the present disclosure will become apparent from the detailed description of the following embodiments in conjunction with the accompanying drawings, in which.

DETAILED DESCRIPTION

Hereinafter, embodiments of the present disclosure will be described in detail. One aspect of the present disclosure relates to a method of preparing digestion-resistant maltodextrin from roasted dextrin, including: introducing activated carbon and reacting the activated carbon with roasted dextrin after saccharification of the roasted dextrin and before filtration of the saccharified roasted dextrin.

Another aspect of the present disclosure relates to a method of preparing digestion-resistant maltodextrin from roasted dextrin, including: a) liquefying roasted dextrin; b) saccharifying the roasted dextrin; c) introducing activated carbon and reacting the activated carbon with the roasted dextrin having been liquefied and saccharified; and d) filtering the reacted roasted dextrin.

Referring to FIG. 1, in a typical method of preparing maltodextrin, after roasted dextrin is saccharified and the saccharified roasted dextrin is filtered, specifically vacuum filtered, activated carbon is added to perform decoloration. In this case, there is a problem in that perlite coated on a vacuum filter can have a considerably reduced filtration rate due to specific fine particles contained in the roasted dextrin, or the fine particles can penetrate the perlite, thereby causing malfunction of the perlite. According to the present disclosure, activated carbon is introduced and reacted with roasted dextrin after saccharification of the roasted dextrin and before filtration of the roasted dextrin, whereby fine particles contained in the roasted dextrin can be removed by the activated carbon so as to prevent reduction in the filtration rate of perlite while maintaining functionality of the perlite in a subsequent filtration process. As such, the activated carbon serves to remove the fine particles contained in the roasted dextrin while providing decoloration.

In some embodiments, the activated carbon may be introduced and reacted with the roasted dextrin after liquefaction and saccharification of the roasted dextrin and before filtration of the saccharified roasted dextrin.

The digestion-resistant maltodextrin includes all kinds of typical digestion-resistant dextrin and may be prepared by, for example, a method disclosed in Korean Patent No. 0235141. However, the method may be partially modified for application to the present disclosure. Digestion-resistant dextrin is a digestion-resistant component fraction of a product obtained through enzymatic decomposition and refinement of roasted dextrin and refers to dextrin having a dietary fiber content of 55% (w/w) to 99% (w/w).

The roasted dextrin, which is a raw material for digestion-resistant maltodextrin herein, is prepared by a process in which an acid such as hydrochloric acid, sulfuric acid, and nitric acid is added to corn starch in a small amount, followed by heating to a temperature of 130° C. to 180° C. subsequent to preliminary drying with hot air. As used herein, the term "roasted dextrin" refers to dextrin which has a degree of polymerization (DE) of 10 to 15 and a dietary fiber content of 35% (w/w) to 50% (w/w), preferably 45% (w/w) to 50% (w/w), as calculated based on the total weight of the composition. The roasted dextrin is mainly yellow or creamy and is also referred to as yellow roasted dextrin.

Liquefaction of the roasted dextrin may include hydrolyzing the roasted dextrin using α-amylase, specifically heat resistant α-amylase. Although a commercially available enzyme may be used as the α-amylase, the α-amylase may be, for example, an enzyme derived from *Bacillus licheniformis*, an enzyme derived from *bacillus* microorganisms, or a heat resistant α-amylase enzyme having hydrolytic efficacy comparable therewith. Specifically, liquefaction of the roasted dextrin may be performed by a process in which after 30 wt % to 35 wt % of the roasted dextrin is dissolved in water to be adjusted to a pH of 5.5 to 6.0, the α-amylase is added in an amount of 0.05 wt % to 10 wt %, specifically 0.05 wt % to 5 wt %, more specifically 0.05 wt % to 0.5 wt % in terms of solid content, followed by reaction at 50° C. to 140° C., specifically at 60° C. to 130° C., more specifically at 90° C. to 110° C. for 30 minutes to 6 hours, specifically for 30 minutes to 5 hours, more specifically 60 minutes to 120 minutes.

Thereafter, the liquefied roasted dextrin may be saccharified. Herein, saccharification refers to a process in which glucoamylase is added to a liquefied solution to hydrolyze decomposable dextrin in the liquefied solution, excluding dietary fibers, into glucose. Besides glucoamylase (for example, enzymes derived from *Aspergillus niger*), any enzyme capable of producing glucose as a final product, such as maltogenase (for example, enzymes derived from *bacillus sterothermophilus*), may be used. Specifically, saccharification of the liquefied roasted dextrin may be performed by a process in which after a liquefied roasted dextrin solution is adjusted to a pH of 4.0 to 6.0, specifically 4.3 to 4.8, glucoamylase is added in an amount of 0.05% (w/v) to 10% (w/v), specifically 0.05% (w/v) to 5% (w/v), more specifically 0.05% (w/v) to 0.5% (w/v), based on the volume of the solution, followed by reaction at 40° C. to 100° C., specifically at 50° C. to 70° C., more specifically at 55° C. to 65° C. for 30 minutes to 6 hours, specifically for 30 minutes to 5 hours, more specifically 60 minutes to 120 minutes. After saccharification, the roasted dextrin may have a degree of polymerization (DE) of 40 to 60, preferably a DE of 45 to 55, most preferably a DE of 48 to 52.

Then, the activated carbon may be added and reacted with the saccharified roasted dextrin.

Before addition of the activated carbon, the saccharified roasted dextrin may be heated to a temperature of 50° C. to 100° C., specifically 60° C. to 90° C., more specifically 70° C. to 75° C. Then, the activated carbon may be added in an amount of 1 wt % to 20 wt %, specifically 2 wt % to 10 wt %, more specifically 5 wt % to 7 wt % based on the weight of the saccharified roasted dextrin. Alternatively, a weight ratio of the roasted dextrin to the activated carbon may range from 10:1 to 30:1. After addition of the activated carbon, a mixture of the roasted dextrin and the activated carbon may be reacted while stirring the mixture at 50° C. to 100° C. for 1 minute to 1 hour, for example, about 30 minutes. The activated carbon may be fine activated carbon having an average particle size of 1 μm to 800 μm, specifically 1 μm to 100 μm. When the activated carbon is reacted with the saccharified roasted dextrin through stirring at high temperature before filtration, specific fine particles contained in the roasted dextrin are adsorbed onto the activated carbon, causing increase in particle size of the activated carbon.

Particle size of the activated carbon before reaction may be 110% to 150%, specifically 120% to 140%, more specifically 130% of the particle size of the activated carbon after reaction.

Then, filtration may be performed to remove the activated carbon. Here, filtration may be performed by at least one of gravity filtration, pressure filtration, vacuum filtration, and centrifugal filtration. Specifically, filtration may be performed by vacuum filtration, more specifically vacuum-drum filtration. Then, filter press filtration may be additionally performed. Filter press filtration is aimed at removing activated carbon having not been filtered out by gravity filtration, pressure filtration, and the like.

Filtration may be performed at a flow rate of 5 m$^3$/hr to 10 m$^3$/hr, preferably 7 m$^3$/hr to 9 m$^3$/hr. If the flow rate is less than the above value, there can be a problem of excessively low process efficiency, whereas if the flow rate exceeds the above value, there is a concern of overload during a continuous process.

Figure 2:
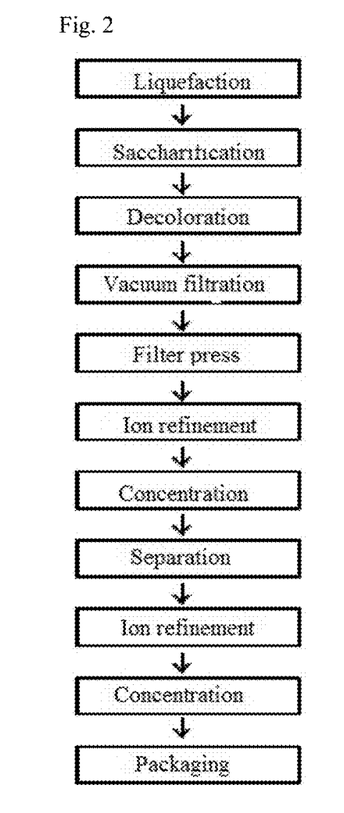
FIG. 2 is a flowchart of a method of preparing digestion-resistant maltodextrin according to one embodiment of the present disclosure.

As described above, according to the present disclosure, fine particles contained in the roasted dextrin can be removed in advance by the activated carbon to prevent reduction in filtration rate and maintain filtration functionality in a subsequent filtration process. FIG. 2 is a flowchart of the method of preparing digestion-resistant maltodextrin according to the embodiment of the disclosure.

After filtration, in order to remove impurities such as colored components and ionic components, the filtered solution is passed, at room temperature, through a column filled with a cation exchange resin, an anion exchange resin, or a mixture of the cation exchange resin and the anion exchange resin at a flow rate of a volume twice that of the ion exchange resin per hour to be desalinized. Then, the solution is adjusted to an amount of 50 wt % through a concentration process, followed by separation of glucose and disaccharides using continuous ion exchange resin chromatography. Through the separation process, the content of glucose and disaccharides may be reduced to 5% or less based on total solids.

Separated tri- or higher saccharides, which have not been decomposed by hydrolysis with liquefaction/saccharification enzymes, are subjected to ion refinement using a mixture of a cation exchange resin and an anion exchange resin and then concentrated to 50 wt % to 55 wt %, followed by spray drying, thereby producing a powdered product, or concentrated to 65 wt %, followed by filtration using an antibacterial filter subsequent to high-temperature short-time (HTST) sterilization, thereby preparing liquefied digestion-resistant maltodextrin.

According to the present disclosure, it is possible to provide a method of preparing digestion-resistant maltodextrin in which activated carbon is introduced to remove fine particles before vacuum filtration so as to effectively reduce consumption of perlite in vacuum filtration and/or filter press filtration, thereby improving filtration rate and efficiency, whereby digestion-resistant maltodextrin can be produced economically.

In addition, according to the present disclosure, it is possible to provide a method of preparing digestion-resistant maltodextrin which can exhibit a filtration rate at the same level as in production of other starch sugar products (5 m$^3$/hr to 10 m$^3$/hr) and effectively reduce consumption of perlite which is a filtration aid, thereby improving productivity and efficiency.

Next, the present disclosure will be described in more detail with reference to examples. However, it should be noted that these examples are provided for illustration only and should not be construed in any way as limiting the disclosure.

Reference Example 1: Change in Particle Size of Activated Carbon According to Decoloration Treatment Roasted dextrin was subjected to high-temperature liquefaction at 100° C. and hydrolysis with a saccharification enzyme at 60° C. and then heated to 70° C. when the roasted dextrin had a DE of 49 or more after completion of reaction. Then, activated carbon was added in an amount of 6 wt % in terms of solid content, followed by stirring for 30 minutes or more. Thereafter, particle size of the activated carbon before/after reaction was measured using a wet particle size analyzer (available from Malvern Instruments) within a range of 0.01 μm to 3000 μm.

Figure 3:
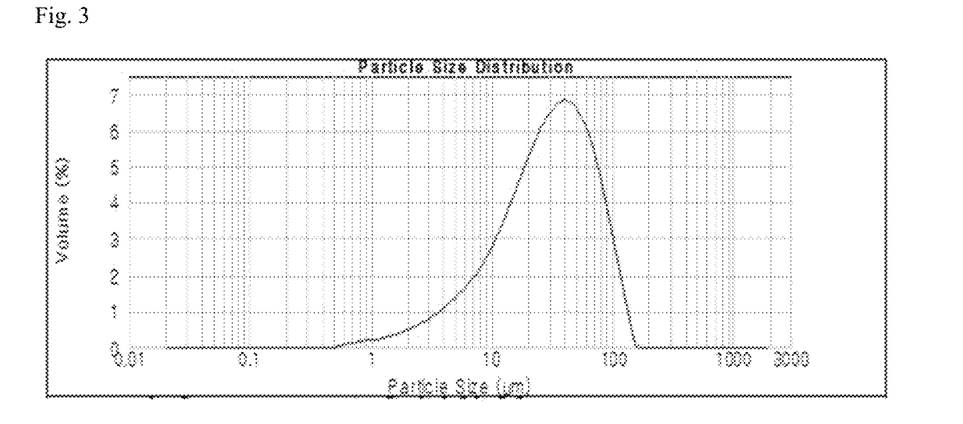
FIG. 3 is a graph showing a wet particle size distribution of activated carbon powder according to one embodiment of the present disclosure.
Figure 4:
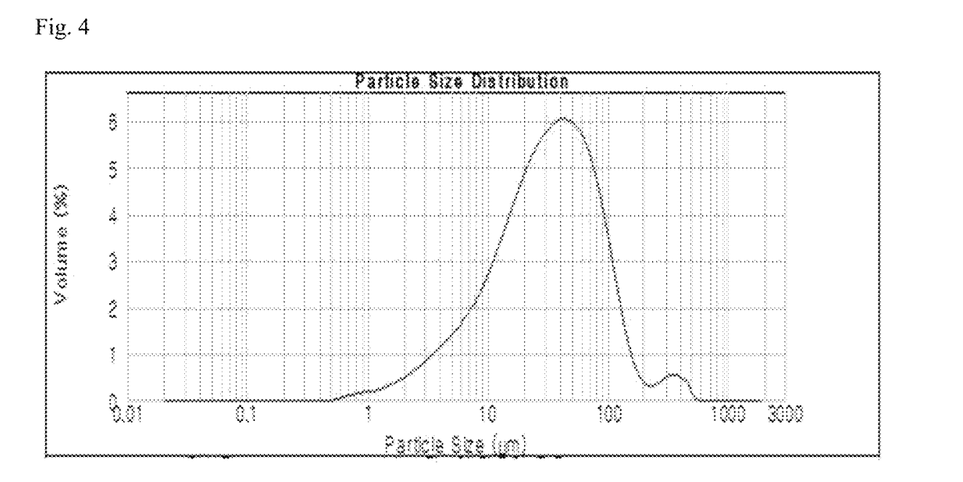
FIG. 4 is a graph showing a wet particle size distribution of activated carbon powder after decoloration according to one embodiment of the present disclosure.

It was confirmed that, after the hydrolyzed roasted dextrin was treated with the activated carbon, the average particle size of the activated carbon was increased by about 30%, as compared with that of the activated carbon before treatment with the activated carbon due to undissolved substances of the roasted dextrin adsorbed onto the activated carbon. FIG. 3 is a graph showing a wet particle size distribution of activated carbon powder before reaction, and FIG. 4 is a graph showing a wet particle size distribution of activated carbon powder after reaction. From the graphs, it can be seen that non-decomposed and undissolved substances disturbing filtration were present in large amounts. When cornstarch is subjected to hydrolysis with an acid, roasted dextrin is produced through a roasting reaction. Here, some cornstarch is not hydrolyzed into dextrin within a reaction time and remains as digestion-resistant starch. Such substances are referred to as non-decomposed and undissolved substances herein and are likely to disturb filtration.

TABLE 1

| Item | Average particle size (μm) | Particle size distribution (μm) | | |
|---|---|---|---|---|
| | | Early section | Middle section | Late section |
| Activated carbon powder | 37.6 | 6.6 | 30.2 | 79.9 |
| Particle size of activated carbon after decoloration (adsorption) | 49.0 | 6.6 | 32.5 | 99.9 |

Figure 7:
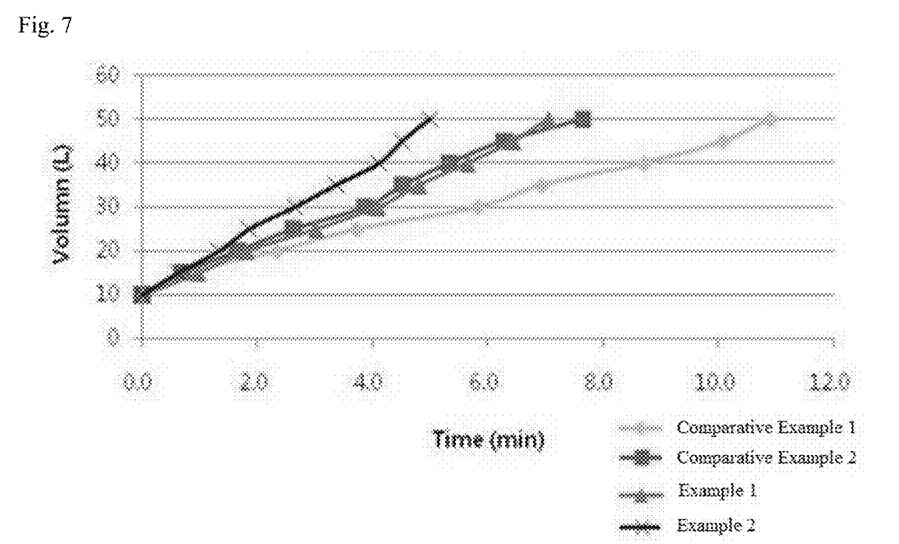
FIG. 7 is a graph showing a filtration rate of a solution under each condition upon operation of a pilot-scale vacuum filter with and without activated carbon treatment of roasted dextrin hydrolyzed at a liquefaction temperature in Examples and Comparative Examples.
Figure 8A:
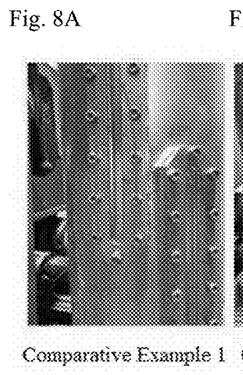
FIGS. 8A to 8D show pictures of bubbles generated when a solution having been subjected to filtration under each condition dropped into a storage tank upon operation of a pilot-scale vacuum filter with and without activated carbon treatment of roasted dextrin hydrolyzed at a liquefaction temperature in Examples and Comparative Examples.
Figure 8B:
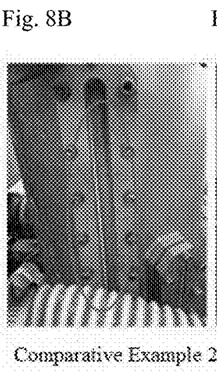
Figure 8C:
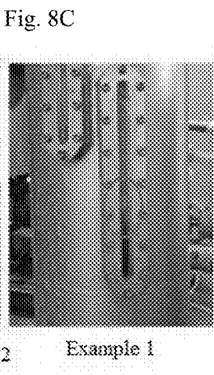
Figure 8D:
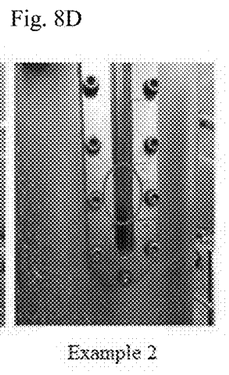
Figure 9A:
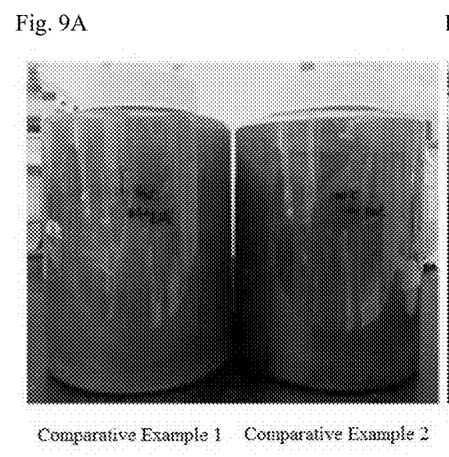
FIG. 9A and FIG. 9B show pictures of a state of a solution having been subjected to filtration under each condition upon operation of a pilot-scale vacuum filter with and without activated carbon treatment of roasted dextrin hydrolyzed at a liquefaction temperature in Examples and Comparative Examples.
Figure 9B:
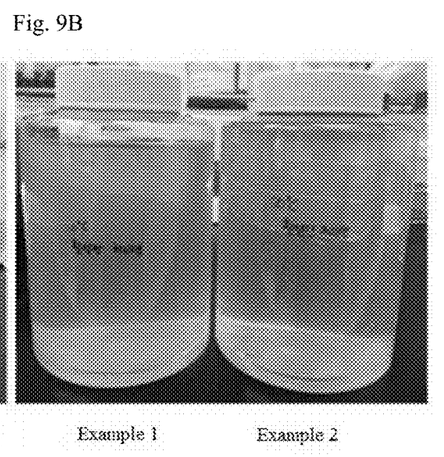
Figure 10:
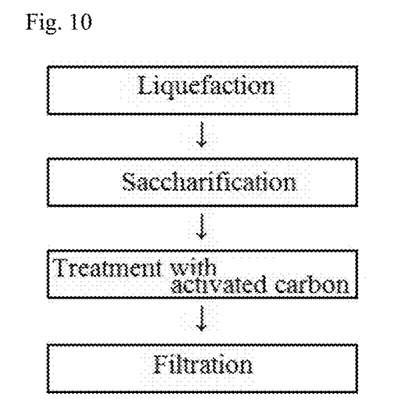
FIG. 10 is a flowchart of a method of preparing digestion-resistant maltodextrin according to one embodiment of the present disclosure.

Comparative Example 1: Middle-Temperature Liquefaction→Saccharification→Vacuum Filtration 50 L of a 30 wt % roasted dextrin solution was adjusted to a pH of 5.8 using NaOH, followed by liquefaction for 2 hours using a middle-temperature liquefying enzyme (BAN, Novozymes Inc.) in an amount of 0.2% in terms of solid content while heating the solution to 60° C. Then, the solution was adjusted to a pH of 4.5 using HCl followed by reaction for 24 hours using a saccharification enzyme (AMG 300L, Novozymes Inc.) in an amount of 0.2% in terms of solid content, and was heated to 70° C. when the roasted dextrin had a DE of 49 or more at the time of completion of reaction. 5 kg of perlite (KF400, Kyungdong Ceratech Co., Ltd.) was coated onto a pilot vacuum filter (filter area: 0.5 m²), followed by measuring the filtration rate of the hydrolyzed roasted dextrin. The measured filtration rate was 4.58 L/min (see Table 2 and FIG. 7). It was confirmed that undissolved substances penetrated a 5 cm thick perlite layer on the vacuum drum filter to a depth of 2.5 cm (to the middle of the perlite layer) (see FIG. 6). In addition, it was confirmed that a large amount of bubbles were generated when a liquid discharged from the vacuum drum filter dropped down (see FIG. 8). Further, a liquid subsequently discharged from the filter was turbid (see FIG. 9).

Comparative Example 2: High-temperature Liquefaction→Saccharification→Vacuum Filtration 50 L of a 30 wt % roasted dextrin solution was adjusted to a pH of 5.8 using NaOH, followed by liquefaction for 2 hours using a high-temperature liquefying enzyme (Liquozyme Supra, Novozymes Inc.) in an amount of 0.2% in terms of solid content while heating the solution to 100° C. Then, the solution was adjusted to a pH of 4.5 using HCl, followed by reaction for 24 hours using a saccharification enzyme (AMG 300 L, Novozymes, Inc.) in an amount of 0.2% in terms of solid content, and was heated to 70° C. when the roasted dextrin had a DE of 49 or more at the time of completion of reaction. 5 kg of perlite (KF400, Kyungdong Ceratech Co., Ltd.) was coated onto a pilot vacuum filter (filter area: 0.5 m²), followed by measuring the filtration rate of the hydrolyzed roasted dextrin. The measured filtration rate was 7.04 L/min (see Table 2 and FIG. 7). It was confirmed that undissolved substances penetrated a 5 cm thick perlite layer on the vacuum drum filter to a depth of 2.5 cm (to the middle of the perlite layer), as in Comparative Example 1 (see FIG. 6). In addition, it was confirmed that a large amount of bubbles were generated when a liquid discharged from the vacuum drum filter dropped down, as in Comparative Example 1 (see FIG. 8). Further, a liquid subsequently discharged from the filter was turbid, as in Comparative Example 1 (see FIG. 9).

Example 1: Middle Temperature Liquefaction-→Saccharification→Introduction of Activated Carbon→Vacuum Filtration 50 L of a 30 wt % roasted dextrin solution was adjusted to a pH of 5.8 using NaOH, followed by liquefaction for 2 hours using a middle-temperature liquefying enzyme (BAN, Novozymes, Inc.) in an amount of 0.2% in terms of solid content while heating the solution to 60° C. Then, the solution was adjusted to a pH of 4.5 using HCl, followed by reaction for 24 hours using a saccharification enzyme (AMG 300L, Novozymes, Inc.) in an amount of 0.2% in terms of solid content, and was heated to 70° C. when the roasted dextrin had a DE of 49 or more at the time of completion of reaction. After completion of heating to 70° C., 0.9 kg of activated carbon was introduced, followed by stirring for 30 minutes. 5 kg of perlite (KF400, Kyungdong Ceratech Co., Ltd.) was coated onto a pilot vacuum filter (filter area: 0.5 m²), followed by measuring the filtration rate of the hydrolyzed roasted dextrin. The measured filtration rate was 6.49 L/min (see Table 2 and FIG. 7). It was confirmed that undissolved substances were adsorbed onto the activated carbon and filtered out by the perlite and thus did not penetrate a 5 cm thick perlite layer on the vacuum drum filter (see FIG. 6). In addition, it was confirmed that, unlike Comparative Examples 1 and 2, a small amount of bubbles were generated when a liquid discharged from the vacuum drum filter dropped down (see FIG. 8). It was thought that specific substances capable of inducing bubbling were adsorbed onto the activated carbon, thereby suppressing generation of bubbles. Further, a liquid subsequently discharged from the filter was not turbid due to decoloration with the activated carbon (see FIG. 9).

Example 2: High-temperature Liquefaction→Saccharification→Introduction of Activated Carbon-→Vacuum Filtration 50 L of a 30 wt % roasted dextrin solution was adjusted to a pH of 5.8 using NaOH, followed by liquefaction for 2 hours using a high-temperature liquefying enzyme (Liquozyme Supra, Novozymes, Inc.) in an amount of 0.2% in terms of solid content while heating the solution to 100° C. Then, the solution was adjusted to a pH of 4.5 using HCl, followed by reaction for 24 hours using a saccharification enzyme (AMG 300 L, Novozymes, Inc.) in an amount of 0.2% in terms of solid content, and was heated to 70° C. when the roasted dextrin had a DE of 49 or more at the time of completion of reaction. After completion of heating to 70° C., 0.9 kg of activated carbon was introduced, followed by stirring for 30 minutes. 5 kg of perlite (KF400, Kyungdong Ceratech Co., Ltd.) was coated onto a pilot vacuum filter (filter area: 0.5 m²), followed by measuring the filtration rate of the hydrolyzed roasted dextrin. The measured filtration rate was 10.0 L/min, the highest value among those of Examples and Comparative Examples (see Table 2 and FIG. 7). It was confirmed that undissolved substances were adsorbed onto the activated carbon and filtered out by the perlite and thus did not penetrate a 5 cm thick perlite layer on the vacuum drum filter, as in Example 1 (see FIG. 6). In addition, it was confirmed that, unlike Comparative Examples 1 and 2, a small amount of bubbles were generated when a liquid discharged from the vacuum drum filter dropped down, as in Example 1 (see FIG. 8). Further, a liquid subsequently discharged from the filter was not turbid due to decoloration with the activated carbon, as in Example 1 (see FIG. 9).

TABLE 2

|  | Comparative example 1 | Comparative example 2 | Example 1 | Example 2 |
|---|---|---|---|---|
| Introduction of activated carbon before vacuum filtration | X | X | ○ | ○ |
| Liquefaction temperature | 60° C. | 100° C. | 60° C. | 100° C. |
| Time for 50 L filtration | 10.9 min | 7.1 min | 7.7 min | 5 min |
| Filtration rate per unit area | 9.2 L/m² min | 14.0 L/m² min | 12.9 L/m² min | 20.0 L/m² min |
| Throughput/min | 4.58 L/min | 7.04 L/min | 6.49 L/min | 10.0 L/min |
| Time for 1 L filtration | 0.218 min | 0.142 min | 0.154 min | 0.1 min |
| Permeability (720 nm, 10Bx) | 1.846 | 1.796 | 0.012 | 0.011 |

Figure 5A:
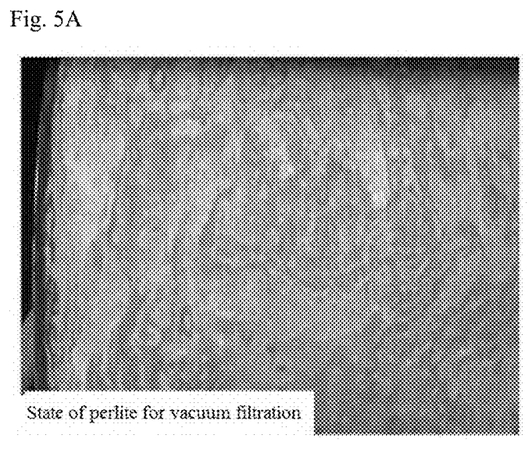
FIG. 5A and FIG. 5B show pictures of a phenomenon wherein perlite coated on a vacuum drum filter lost filtration ability and was easily scratched by a finger upon primary filtration of enzymatically hydrolyzed roasted dextrin through vacuum drum filtration in a comparative example.
Figure 5B:
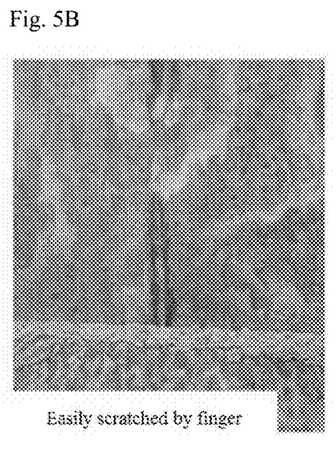
Figure 6A:
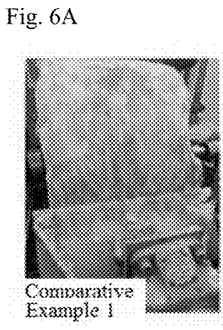
FIGS. 6A to 6D show pictures of a middle layer of a perlite layer upon operation of a pilot-scale vacuum filter with and without activated carbon treatment of roasted dextrin hydrolyzed at a liquefaction temperature in Examples and Comparative Examples.
Figure 6B:
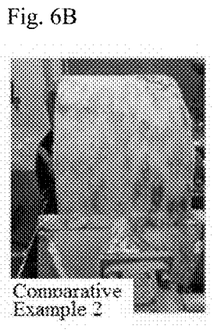
Figure 6C:
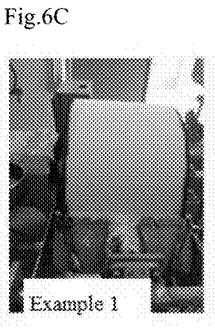
Figure 6D:
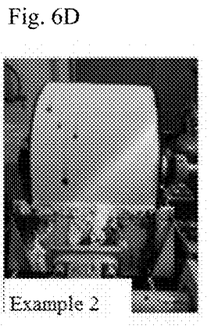

Comparative Example 3: Saccharification→Vacuum Drum Filtration→Introduction of Activated Carbon 32 t of roasted dextrin was introduced into a 100 m³ saccharification tank to prepare a solution of 32 wt % roasted dextrin, and the solution was adjusted to a pH of 5.8 using 50 wt % NaOH while heating to 60° C. Then, liquefaction was performed for 2 hours using a middle-temperature liquefying enzyme (BAN, Novozymes, Inc.) in an amount of 0.2% in terms of solid content, and the solution was adjusted to a pH of 5.8 using 4 wt % HCl, followed by saccharification using amyloglucosidase (AMG 300 L, Novozymes Inc.) in an amount of 0.2% in terms of solid content. The solution was heated to 70° C., a temperature suitable for filtration, when the roasted dextrin had a DE of 49 or more at the time of completion of saccharification and was passed through a vacuum drum filter. Filtration through perlite (KF400, Kyungdong Ceratech Co., Ltd.) coated on the vacuum drum filter was disturbed due to undissolved substances, and the perlite was easily scratched by a finger (see FIG. 5). Then, the solution was diluted to 20 wt % and passed through the vacuum drum filter at a flow rate of 1 m³/hr to 2 m³/hr. Thereafter, the perlite of the vacuum drum filter was replaced 5 times (i.e. was coated onto the vacuum drum filter 6 times in total), thereby performing primary vacuum drum filtration. Then, 1.92 t of activated carbon was added to a solution having passed through the vacuum drum filter, followed by stirring for 30 minutes, and secondary filtration was performed using a filter press filled with fine perlite (KF150, Kyungdong Ceratech Co., Ltd.). In secondary filtration, cleaning of the filter press was performed 4 times and 0.48 t of perlite was consumed (see Table 3).

Example 3: Saccharification→Introduction of Activated Carbon→Vacuum Drum Filtration 32 t of roasted dextrin was introduced into each of three 100 m³ saccharification tanks to prepare a solution of 32 wt % roasted dextrin, and the solution was adjusted to a pH of 5.8 using 50 wt % NaOH while heating to 105° C. Then, liquefaction was performed for 2 hours using a high-temperature liquefying enzyme (Liquozyme Supra, Novozymes Inc.) in an amount of 0.2% in terms of solid content, and the solution was adjusted to a pH of 4.5 using 4 wt % HCl, followed by saccharification for 24 hours using amyloglucosidase (AMG 300L, Novozymes Inc.) in an amount of 0.2% in terms of solid content. The solution was heated to 70° C., a temperature suitable for filtration, when the roasted dextrin had a DE of 49 or more at the time of completion of saccharification, followed by decoloration for 30 minutes using 5.7 t of activated carbon. After completion of decoloration, the solution was passed through a vacuum drum filter. Here, a flow rate of the solution through the vacuum drum filter was 7 m³/hr to 9 m³/hr, and perlite was not replaced. Then, secondary filtration was performed at a flow rate of 7 m³/hr to 9 m³/hr using a filter press without replacement of perlite (see Table 3).

Example 4: Saccharification→Introduction of Activated Carbon→Vacuum Drum Filtration 30 t of roasted dextrin was introduced into each of three 100 m³ saccharification tanks to prepare a solution of 30 wt % roasted dextrin, and the solution was adjusted to a pH of 5.8 using 50 wt % NaOH while heating to 105° C. Then, liquefaction was performed for 2 hours using a high-temperature liquefying enzyme (Liquozyme Supra, Novozymes Inc.) in an amount of 0.2% in terms of solid content, and the solution was adjusted to a pH of 4.5 using 4 wt % HCl, followed by saccharification for 24 hours using amyloglucosidase (AMG 300L, Novozymes, Inc.) in an amount of 0.2% in terms of solid content. The solution was heated to 70° C., that is, a temperature suitable for filtration, when the roasted dextrin had a DE of 49 or more at the time of completion of saccharification, followed by decoloration for 30 minutes using 7.2 t of activated carbon. After completion of decoloration, the solution was passed through a vacuum drum filter. Here, a flow rate of the solution through the vacuum drum filter was 7 m³/hr to 9 m³/hr, and perlite was not replaced. Then, secondary filtration was performed at a flow rate of 7 m³/hr to 9 m³/hr using a filter press without replacement of perlite. Consumption of the raw material and consumption of the activated carbon were increased by 25% and 26.2%, respectively, as compared with those of Example 3, and the flow rate of the solution through the vacuum drum filter and the number of replacement times were the same as in Example 3 (see Table 3).

TABLE 3

|  | Comparative Example 3 | Example 3 | Example 4 |
|---|---|---|---|
| Amount of raw material | 32 t | 96 t | 120 t |
| Liquefaction temperature | 60° C. | 100° C. | 100° C. |
| Introduction of activated carbon before vacuum filtration | X | ◯ | ◯ |
| Amount of activated carbon added before vacuum filtration | — | 5700 kg | 7200 kg |
| Filtration rate per hour | 1 to 2 m³/hr | 7 to 9 m³/hr | 7 to 9 m³/hr |
| Number of operations of coating perlite on vacuum drum filter | 6 | 1 | 1 |
| Total consumption of perlite of vacuum drum filter | 3200 kg | 530 kg | 530 kg |
| Number of operations of coating perlite on filter press | 4 | 1 | 1 |
| Total consumption of perlite of filter press | 480 kg | 120 kg | 120 kg |

What is claimed is:

1. A method of preparing digestion-resistant maltodextrin from roasted dextrin, comprising:
   a) liquefying roasted dextrin;
   b) saccharifying the roasted dextrin;
   c) heating the liquefied and saccharified roasted dextrin to a temperature of 60° C. to 90° C. and introducing activated carbon to remove fine particles from the roasted dextrin, wherein the amount of activated carbon is 5 wt % to 7 wt % based on the weight of the roasted dextrin; and
   d) filtering the roasted dextrin from which the fine particles have been removed,
   wherein the filtration step is performed by filter press filtration with a perlite filter after vacuum filtration at a flow rate of 7 m³/hr to 9 m³/hr and wherein the removal of the fine particles reduces an amount of perlite used in the filter press filtration.

2. The method of preparing digestion-resistant maltodextrin from roasted dextrin according to claim 1, wherein the filtration step further comprises at least one filtration selected from the group consisting of gravity filtration, press filtration, and centrifugal filtration.

3. The method of preparing digestion-resistant maltodextrin from roasted dextrin according to claim 1, wherein liquefying the roasted dextrin comprises hydrolyzing the roasted dextrin at 50° C. to 140° C. for 30 minutes to 6 hours using α-amylase.

4. The method of preparing digestion-resistant maltodextrin from roasted dextrin according to claim 1, wherein saccharifying the roasted dextrin comprises saccharifying the roasted dextrin at 40° C. to 100° C. for 30 minutes to 6 hours using glucoamylase or maltogenase.

5. The method of preparing digestion-resistant maltodextrin from roasted dextrin according to claim 1, wherein introducing the activated carbon to remove fine particles from the roasted dextrin comprises stirring at 50° C. to 100° C. for 1 minute to 1 hour.

6. The method of preparing digestion-resistant maltodextrin from roasted dextrin according to claim 1, wherein a particle size of the activated carbon after the removal of fine particles is 110% to 150% that of the activated carbon before the removal of fine particles.

7. The method of preparing digestion-resistant maltodextrin from roasted dextrin according to claim 1, wherein the liquefied and saccharified roasted dextrin has a DE of 40 to 60.

* * * * *